United States Patent
Karlsson et al.

(10) Patent No.: US 11,679,049 B2
(45) Date of Patent: Jun. 20, 2023

(54) SPLIT DRUM FOR LIFT STRAP IN CEILING STRAP

(71) Applicant: Liko Research & Development AB, Luleå (SE)

(72) Inventors: Roger Karlsson, Rosvik (SE); Mattias Andersson, Södra Sunderbyn (SE); Lars Eklof, Luleå (SE); Laetitia Gazagnes, Montpellier (FR); Josh Shenk, Batesville, IN (US)

(73) Assignee: Liko Research & Development AB, Luleå (SE)

( * ) Notice: Subject to any disclaimer, the term of this patent is extended or adjusted under 35 U.S.C. 154(b) by 372 days.

(21) Appl. No.: 16/838,537

(22) Filed: Apr. 2, 2020

(65) Prior Publication Data

US 2020/0230006 A1 Jul. 23, 2020

Related U.S. Application Data

(60) Continuation of application No. 15/712,500, filed on Sep. 22, 2017, now Pat. No. 10,646,392, which is a division of application No. 14/210,974, filed on Mar. 14, 2014, now abandoned.

(60) Provisional application No. 61/784,073, filed on Mar. 14, 2013.

(51) Int. Cl.
*A61G 7/10* (2006.01)
*A61B 46/20* (2016.01)

(52) U.S. Cl.
CPC ......... *A61G 7/1073* (2013.01); *A61G 7/1015* (2013.01); *A61G 7/1044* (2013.01); *A61G 7/1061* (2013.01); *A61B 2046/205* (2016.02); *Y10T 442/2525* (2015.04)

(58) Field of Classification Search
CPC .. A61G 7/1015; A61G 7/1044; A61G 7/1061; A61G 7/1073; A61B 2046/205; B66D 3/18; B66D 3/20; B66D 3/26; B66D 2700/0183; B66D 2700/0191
See application file for complete search history.

(56) References Cited

U.S. PATENT DOCUMENTS

| | | | |
|---|---|---|---|
| 2,272,778 A | 2/1942 | Reuter |
| 2,350,120 A | 5/1944 | Lawler |
| 2,368,390 A | 1/1945 | Winter |
| 3,501,341 A | 3/1970 | Spange et al. |
| 3,506,985 A | 4/1970 | Lang |

(Continued)

FOREIGN PATENT DOCUMENTS

| | | | | |
|---|---|---|---|---|
| CN | 1409689 A | * | 4/2003 | ............... B66D 1/12 |
| EP | 1452478 A1 | | 9/2004 | |

(Continued)

OTHER PUBLICATIONS

Jun. 11, 2014 European Search Report for European Patent Application No. 14160110.4.

*Primary Examiner* — David R Hare
(74) *Attorney, Agent, or Firm* — Dinsmore & Shohl LLP

(57) ABSTRACT

A patient lift system includes a lift housing, a base lift strap having a first end coupled to a lift housing and a second end coupled to a sling bar. The base lift strap is infection controlled. In one embodiment, a protective sleeve covers the base lift strap, wherein the protective sleeve has a first end and a second end. In another embodiment, the base lift strap is chemically treated to provide infection control.

12 Claims, 11 Drawing Sheets

(56) References Cited

U.S. PATENT DOCUMENTS

| | | | |
|---|---|---|---|
| 3,730,176 A | 5/1973 | Miller | |
| 3,865,104 A | 2/1975 | Paulson | |
| 4,000,533 A | 1/1977 | Higgs | |
| 4,084,275 A | 4/1978 | Ilon | |
| 4,202,064 A * | 5/1980 | Joergensen | B66C 17/00 |
| | | | 212/312 |
| 4,243,118 A | 1/1981 | Landry | |
| 4,243,147 A | 1/1981 | Twitchell et al. | |
| 4,372,452 A | 2/1983 | McCord | |
| 4,634,141 A | 1/1987 | Hagan et al. | |
| 4,905,710 A | 3/1990 | Jones | |
| 5,072,840 A | 12/1991 | Asakawa et al. | |
| 5,122,904 A | 6/1992 | Fujiwara | |
| 5,337,908 A | 8/1994 | Beck | |
| 5,433,221 A | 7/1995 | Adair | |
| 5,456,655 A | 10/1995 | Morris | |
| 5,511,256 A * | 4/1996 | Capaldi | A61G 7/1051 |
| | | | 403/217 |
| 5,524,304 A | 6/1996 | Shutes | |
| 5,669,390 A | 9/1997 | McCormick | |
| 5,694,654 A | 12/1997 | Roy | |
| 5,970,980 A | 10/1999 | Adair | |
| 6,079,062 A | 6/2000 | Mullin | |
| 6,085,368 A | 7/2000 | Robert et al. | |
| 6,123,080 A | 9/2000 | Mohan | |
| 6,637,610 B1 | 10/2003 | Cheeseboro | |
| 6,805,453 B2 | 10/2004 | Spetzler et al. | |
| 6,923,394 B2 | 8/2005 | Goldstein | |
| 7,237,491 B2 | 7/2007 | Faucher et al. | |
| 7,240,621 B2 | 7/2007 | Chepurny et al. | |
| 7,490,634 B2 | 2/2009 | Resendez et al. | |
| 7,600,540 B2 | 10/2009 | Resendez et al. | |
| 7,618,223 B1 | 11/2009 | Begley | |
| 7,634,825 B2 | 12/2009 | Chepurny et al. | |
| 7,727,244 B2 | 6/2010 | Orban, III et al. | |
| 7,883,634 B2 | 2/2011 | Thompson et al. | |
| 7,945,975 B2 | 5/2011 | Thomas et al. | |
| 8,128,068 B2 | 3/2012 | Chepurny et al. | |
| 8,286,637 B2 | 10/2012 | Kaska | |
| 8,444,515 B2 | 5/2013 | Baranda et al. | |
| 9,421,140 B2 * | 8/2016 | Faucher | A61G 7/1015 |
| 9,563,045 B2 | 2/2017 | Doi | |
| 9,855,178 B2 | 1/2018 | Rogers | |
| 9,925,107 B2 | 3/2018 | Faucher et al. | |
| 10,010,468 B2 * | 7/2018 | Duquette | A61G 7/1078 |
| 10,080,693 B1 | 9/2018 | Scheenstra et al. | |
| 10,080,694 B1 | 9/2018 | Scheenstra et al. | |
| 10,335,328 B2 | 7/2019 | Scheenstra et al. | |
| 2003/0092524 A1 | 5/2003 | Baranda et al. | |
| 2004/0075007 A1 | 4/2004 | Goldstein | |
| 2005/0115914 A1 | 6/2005 | Chepurny et al. | |
| 2006/0002252 A1 | 1/2006 | Faucher et al. | |
| 2006/0076024 A1 | 4/2006 | Duarte | |
| 2006/0150987 A1 | 7/2006 | Dillon et al. | |
| 2006/0253977 A1 * | 11/2006 | Hjort | A61G 7/1042 |
| | | | 5/85.1 |
| 2007/0267084 A1 | 11/2007 | Pereira et al. | |
| 2009/0199335 A1 * | 8/2009 | Guldmann | A61G 7/1015 |
| | | | 5/87.1 |
| 2010/0064432 A1 * | 3/2010 | Duquette | A61G 7/1015 |
| | | | 5/88.1 |
| 2010/0270252 A1 * | 10/2010 | Chepurny | A61G 7/1061 |
| | | | 212/76 |
| 2011/0166485 A1 | 7/2011 | Owens | |
| 2011/0277236 A1 * | 11/2011 | Moriarity | A61G 7/1015 |
| | | | 5/87.1 |
| 2013/0019401 A1 | 1/2013 | Faucher et al. | |
| 2013/0167847 A1 | 7/2013 | Rogers | |
| 2014/0075669 A1 * | 3/2014 | Andersson | A61G 7/1051 |
| | | | 192/76 |
| 2014/0259391 A1 | 9/2014 | Karlsson et al. | |
| 2015/0321031 A1 | 11/2015 | Monn | |
| 2016/0006251 A1 | 1/2016 | Modeer et al. | |
| 2018/0008496 A1 | 1/2018 | Karlsson et al. | |

FOREIGN PATENT DOCUMENTS

| | | | | |
|---|---|---|---|---|
| EP | 2649974 A1 | 10/2013 | | |
| EP | 2777674 A1 | 9/2014 | | |
| EP | 3087965 A1 * | 11/2016 | | A61G 7/1015 |
| EP | 3087965 A1 | 11/2016 | | |
| GB | 2231500 A | 11/1990 | | |
| GB | 2431631 A * | 5/2007 | | A61G 7/1015 |
| WO | WO-2005084602 A1 * | 9/2005 | | A61G 7/1042 |
| WO | 2006085881 A1 | 8/2006 | | |
| WO | 2008029272 A2 | 3/2008 | | |
| WO | 2010030879 A1 | 3/2010 | | |

\* cited by examiner

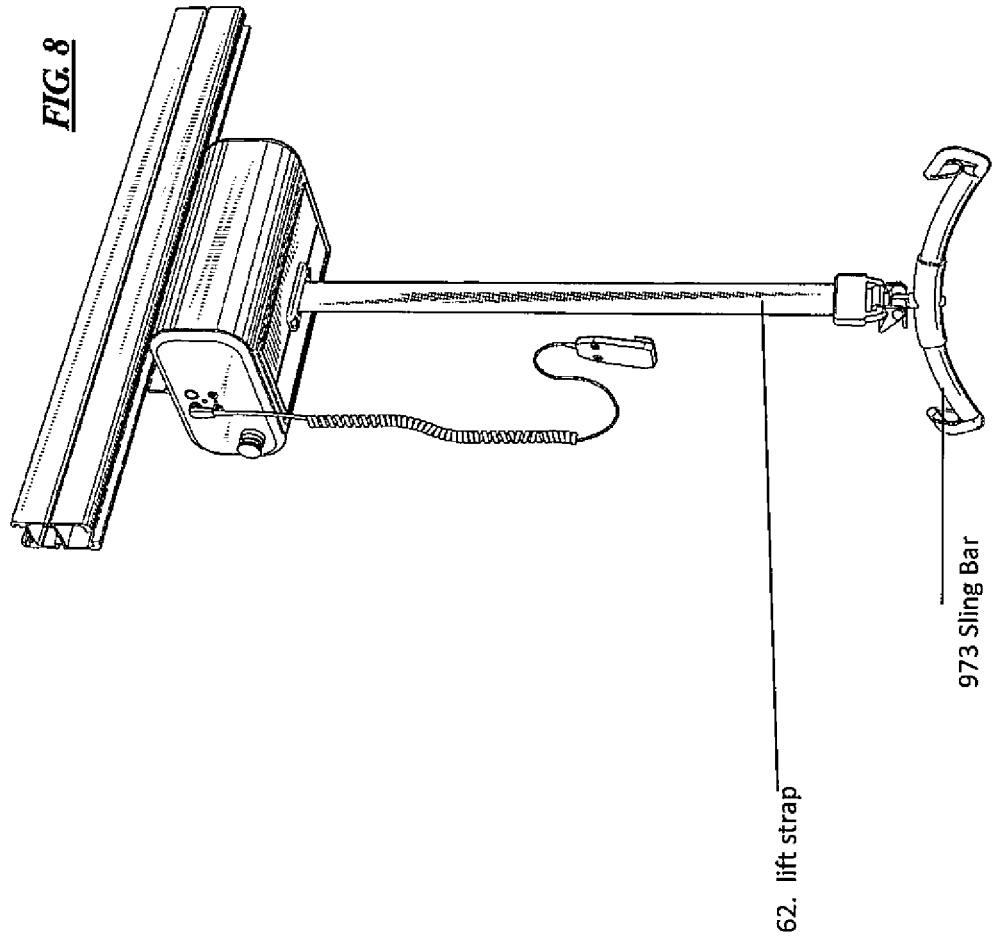

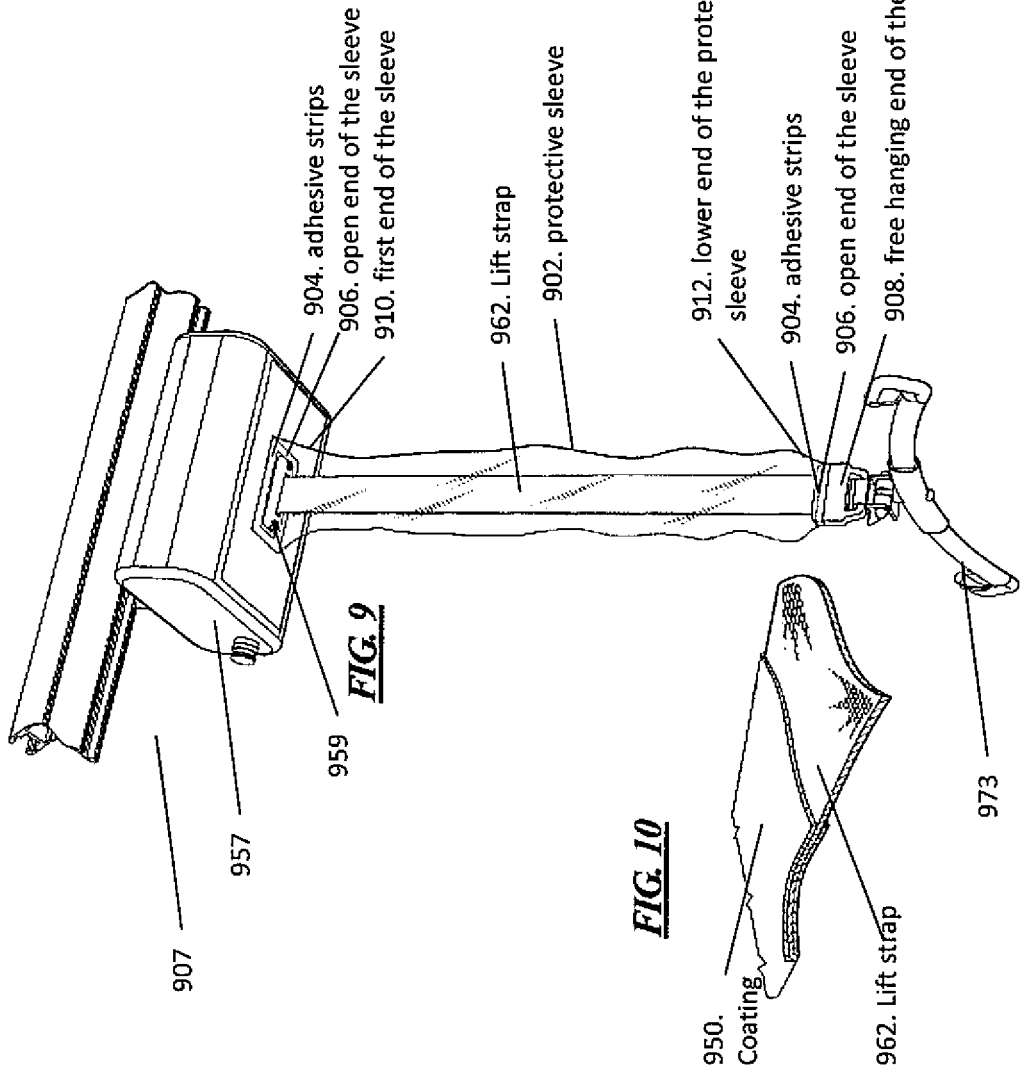

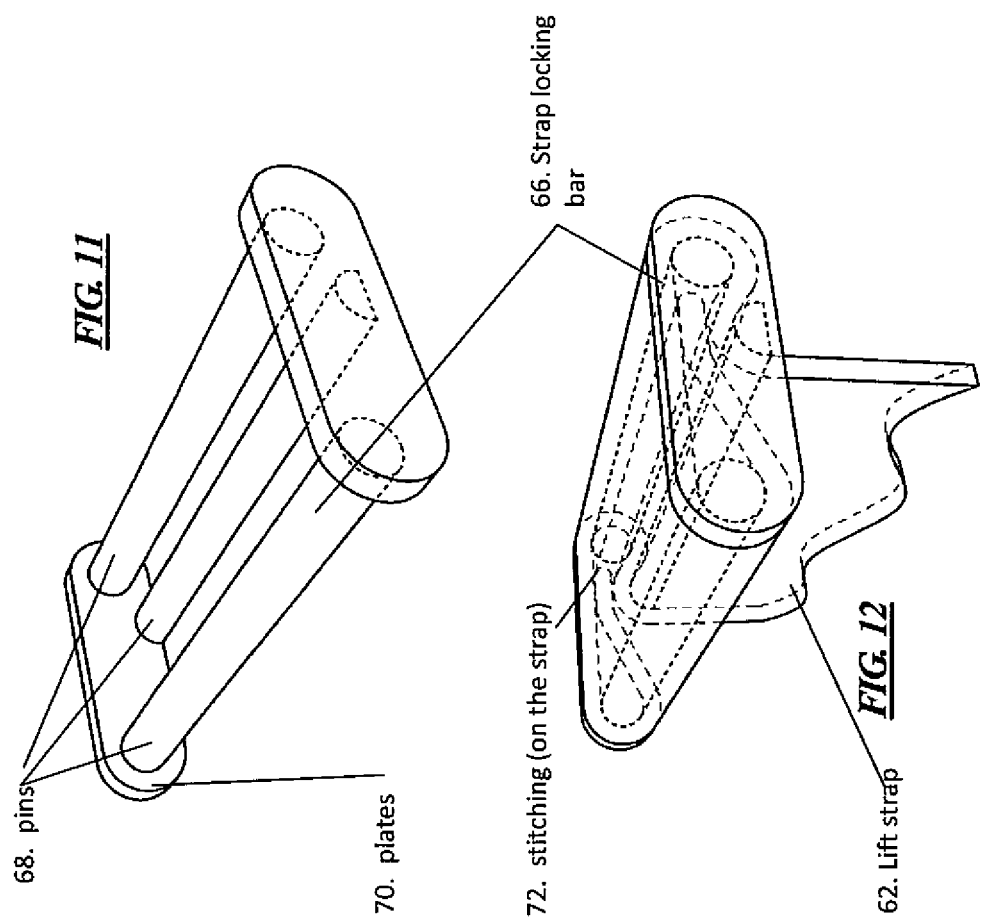

SPLIT DRUM FOR LIFT STRAP IN CEILING STRAP

FIELD

This disclosure relates to overhead patient lift systems.

BACKGROUND

Motorized overhead patient lift systems are known for use in connection with lift straps, sling bars and patient lift slings to lift and transport patients for any number of reasons. The majority of such motorized overhead lift systems typically operate like a winch and usually include a lift motor, a cylindrical lift drum driven by the lift motor, a housing for enclosing the motor and lift drum, and a lift strap affixed at one end within the lift drum for lifting or lowering a patient when the drum is rotated and the strap is respectfully either wound up on the lift drum or paid out from the lift drum. The lift drum of a typical overhead lift system is generally a solid, one-piece cylinder having a central axis of rotation, a cylindrical outer work surface around which the lift strap is wrapped, circular end flanges at each end of the drum, and a strap retention slot for retaining an end of lift strap therein.

However, over time, lift straps wear out from excessive use as well as deterioration caused by the cleaning and disinfecting, or sanitization, process used to prevent bacterial growth on the lift straps. For example, the majority of hospitals that use overhead patient lift systems require that the lift strap be cleaned and disinfected daily or between patient uses. The cleaning and disinfecting, or sanitization, process required by hospitals typically involves the application of chlorinated bleach to the textile lift strap, which lift strap is typically a woven polyester lift strap similar to those used for automobile seat belts. When the chlorinated bleach on the lift strap dries, solid crystals of chlorine are left embedded in the woven fibers of the textile lift strap. Over time, these chlorine crystals build up and deteriorate, or break down, the lift strap's woven fibers, thus reducing the maximum tensile strength of the lift strap and reducing the amount of the active load that can safely be carried by the lift strap.

Accordingly, lift straps often need to be replaced after a certain amount of time or upon signs of excessive wear from use and cleaning. When replacement of the lift strap is necessary, it is often a difficult, tedious, and time consuming process to do so. Most overhead lifts hang from guiderails mounted to the ceiling and are located at a height well above the reach of most individuals. Thus, to replace the lift strap safely and avoid the need for prolonged work while standing on a ladder or working overhead, the entire lift itself must usually be removed from the guide rail system so that replacement of the lift strap can be performed while the lift is on a work table or the like. Due to the weight of the overhead lift, and the need for it to be held securely in the overhead rail system anchored to the ceiling when in use, such removal of the overhead lift is not particularly easy and presents the chance to inadvertently drop the lift from a fairly high height.

Also, because the lift drum is fixed within the outer housing, replacing a lift strap usually involves the removal of at least one end of the outer housing (if not the entire outer housing). It also usually requires removal of the strap guide slot that is fastened to the bottom side of the housing and through which the strap safely enters or exits the interior of the outer housing. Replacement of the lift strap also requires removal the fixed end of the lift strap from its affixed position inside of the lift drum. Often times, this process may further require the removal of numerous screws, fasteners, and extraneous parts, the disconnection of various electrical connections, such as limiting switches or other safety features, the accounting for all removed parts, and the recalling of the proper assembly order of the aforementioned parts so that the lift can be correctly reassembled.

Accordingly, there is a need for a lift system that provides a quicker and easier way to gain access to the lift drum for lift strap replacement, as well as an easier way to remove and replace the lift strap, without needing to go through such a tedious and time consuming process as is currently required to replace such a lift strap for an overhead lift.

In addition, there is a need to either (1) provide an improved infection control lift strap, such that it is easier to clean and will not be subject to premature wear caused by the cleaning process, or (2) better prevent bacteria and other contaminants from reaching the lift strap, and therefore, reducing the frequency with which such harsh cleaning and sanitization procedures need to be performed. By achieving either of these goals, the usable life of the lift strap can be extended beyond that which is currently experienced.

BRIEF DESCRIPTION OF THE DRAWINGS

The present invention is described in detail below with reference to the attached drawing figures, wherein:

FIG. 8 is an isometric view of an embodiment of an overhead lift system of the present disclosure utilizing a split lift drum as disclosed herein, and showing an embodiment of an access door in a bottom of the lift housing in a closed position.

FIG. 9 is an isometric view of an embodiment of an overhead lift system of the present disclosure, and showing an embodiment of an infection control protective sleeve installed over the lift strap of the overhead lift system, secured at the top end of the sleeve to a lift housing and at the bottom end of the sleeve to a lift strap fastener.

FIG. 10 is an isometric cross section view of an infection control coated lift strap of the present disclosure.

FIG. 11 is an isometric view of the embodiment of the lift strap locking bar as shown in FIG. 6.

FIG. 12 is an isometric view of the embodiment of the lift strap locking bar of FIG. 11 secured to the end of a lift strap.

DETAILED DESCRIPTION

Various embodiments now will be described more fully hereinafter with reference to the accompanying drawings, which form a part hereof, and which show, by way of illustration, specific embodiments. However, this invention may be embodied in many different forms and should not be construed as limited to the embodiments set forth herein. Rather, these embodiments are provided so that this disclosure will be thorough and complete, and will fully convey the scope of the invention to those skilled in the art. The following detailed description is not to be taken in a limiting sense.

Throughout the specification and claims, the following terms take the meanings explicitly associated herein, unless the context clearly dictates otherwise. The phrase "in one embodiment" does not necessarily refer to the same embodiment, although it may. Furthermore, the phrase "in another embodiment" does not necessarily refer to a different embodiment, although it may. Thus, as described below, various embodiments may be readily combined without departing from the scope or spirit of the present disclosure.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Figure 1:
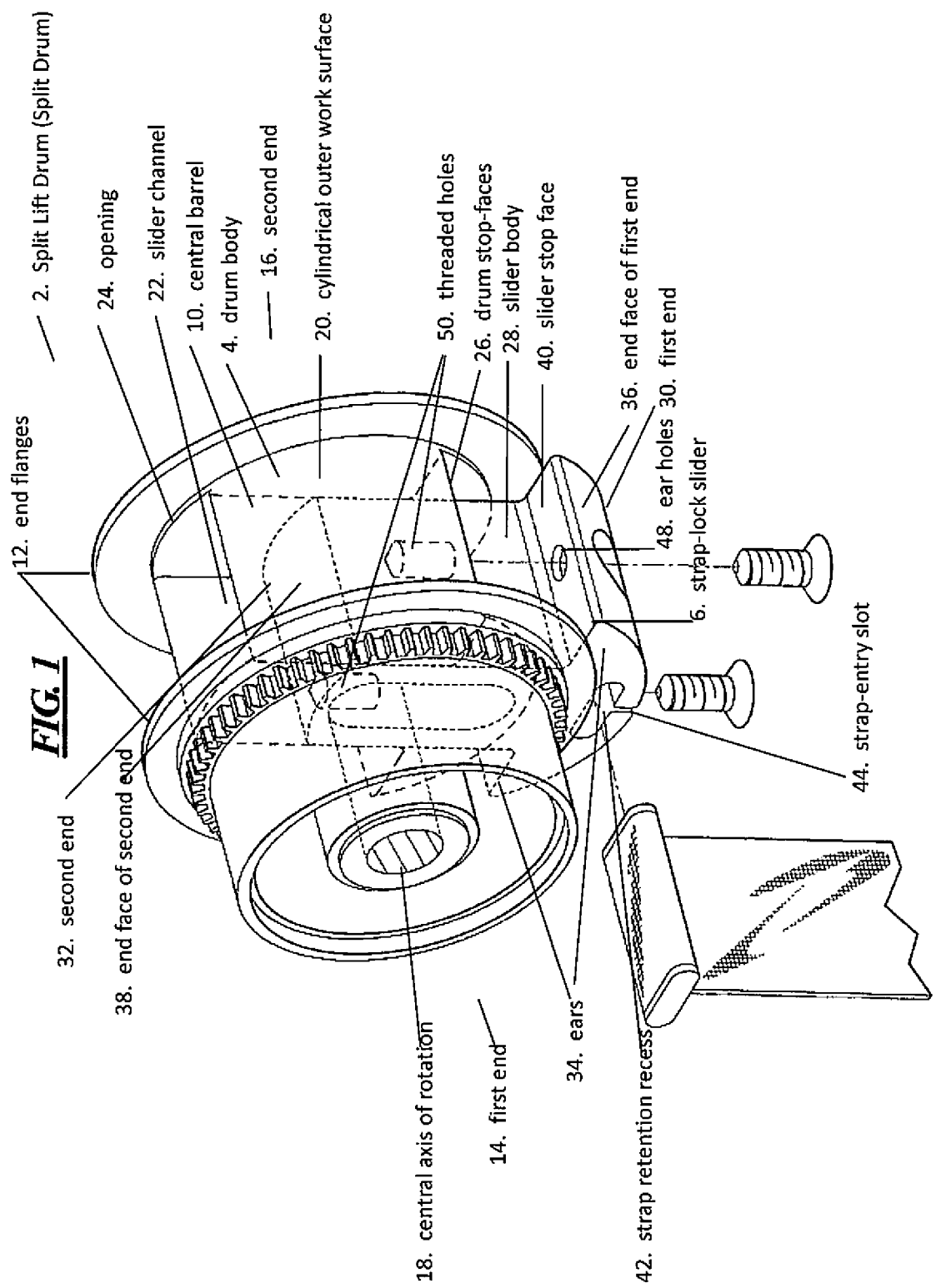
FIG. 1 is an isometric view of an embodiment of a split lift drum of the present disclosure, showing the strap-lock slider in an extended position and a new lift strap being installed therein.
Figure 2:
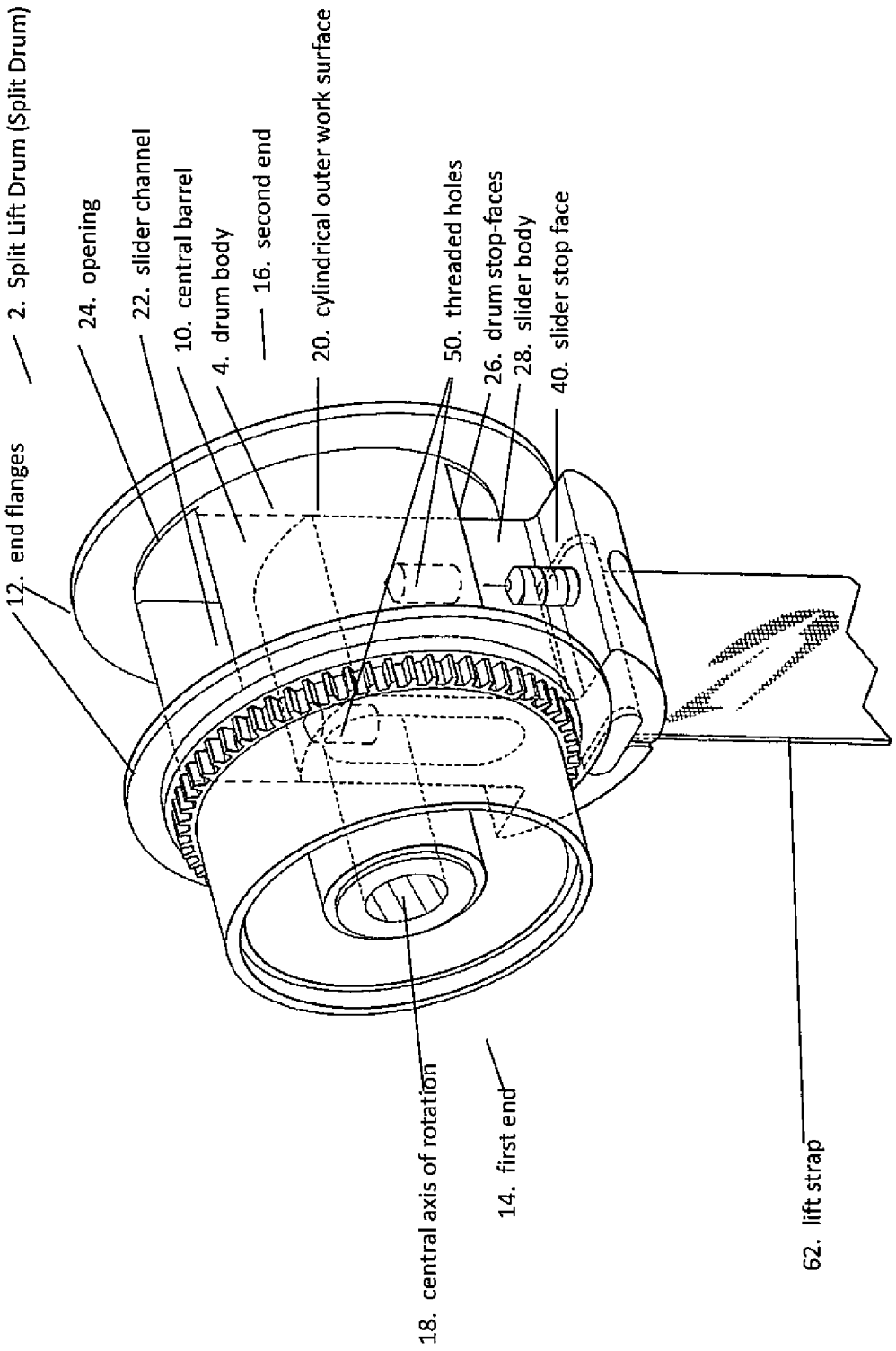
FIG. 2 is an isometric view of the embodiment of the split lift drum of FIG. 1, showing the strap-lock slider in an extended position from the drum body and the replacement lift strap installed therein.
Figure 3:
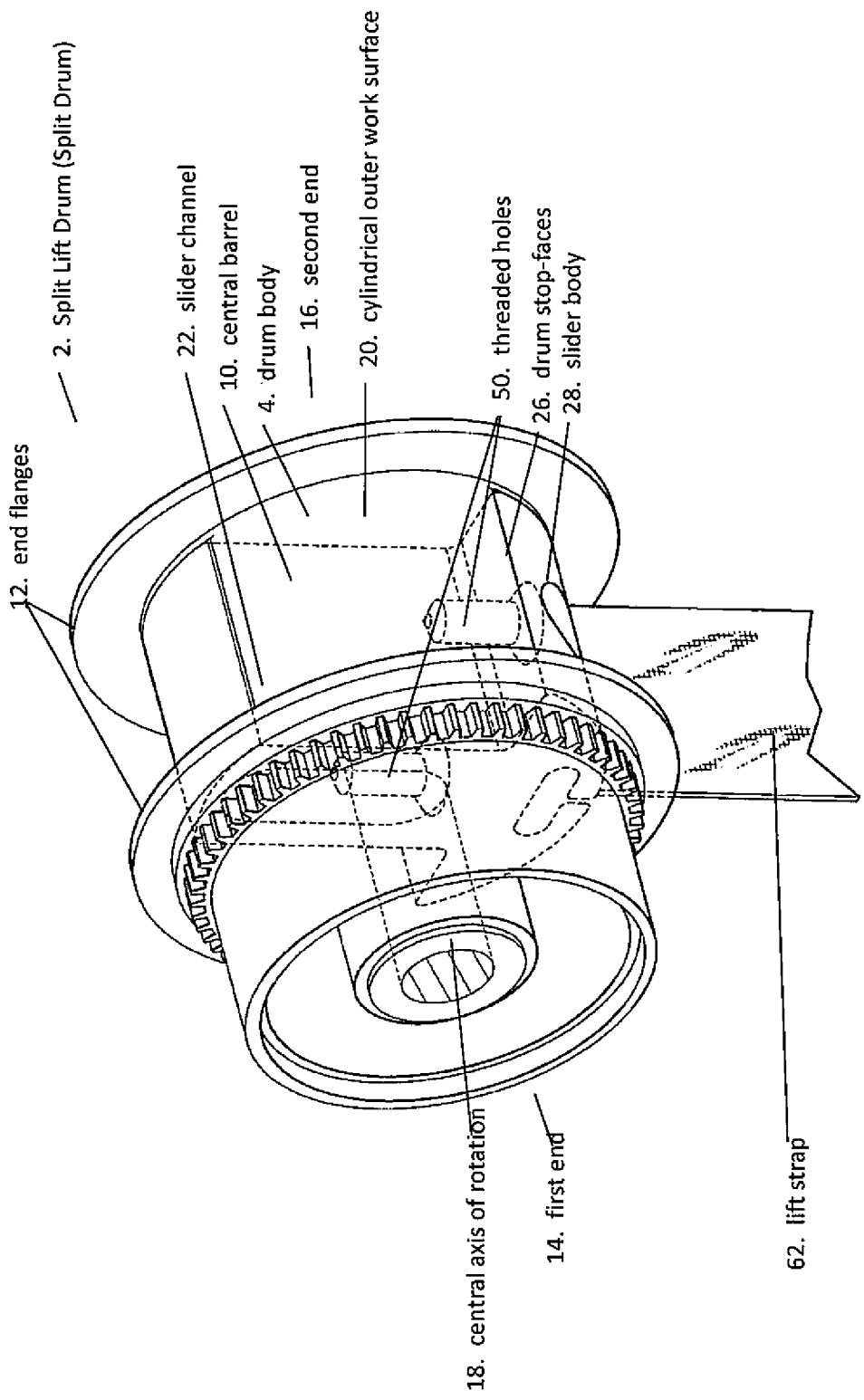
FIG. 3 is an isometric view of the embodiment of the split lift drum of FIG. 1, showing the strap-lock slider and installed lift strap in the fully mated and secured position within the drum body, ready for use in an overhead lift system.

Referring to FIG. 1, an embodiment of a split lift drum, or split drum 2, for use in winding up and paying out a lift strap in a ceiling mounted patient lift is shown. The split drum 2 comprises at least a drum body 4, a strap-lock slider 6 that is slidably engaged within the drum body 4, and one or more fasteners 8 for affixing the strap-lock slider 6 in a fully seated position within the drum body 4.

Drum Body

Referring to FIGS. 1-4, the drum body 4 is generally shaped like a circular cylindrical spool, in that it has a circular cylindrical central barrel 10, end flanges 12 disposed at each of a first end 14 and second end 16 of the central barrel 10, a central axis of rotation 18, and a circular cylindrical outer work surface 20 disposed on the exterior of the central barrel 10, around which a lift strap 62 will be wrapped during use of the split drum 2. The outer diameter of each end flange 12 is larger than the outer diameter of the central barrel 10, so as to properly guide a lift strap around the work surface 20 of the central barrel 10 when the lift strap is being wound up on the split drum 2. The larger diameter end flanges 12 also serve to keep the lift strap 62 centered on the work surface 20 between the end flanges 12 of the split drum 2 and prevent the lift strap 62 from sliding off of the split drum 2.

The drum body 4 also includes a slider channel 22 formed in the central barrel 10 of the drum body 4 to permit the strap-lock slider 6 to be slidably mated therein. The slider channel 22 is generally a radial channel that is disposed transverse to the central axis 18 and defines at least one opening 24 in the exterior work surface 20 of the central barrel 10. The opening 24 defined in the work surface 20 by the slider channel 22 forms a break in the otherwise continuous cylindrical outer work surface 20 of the central barrel.

Figure 4:
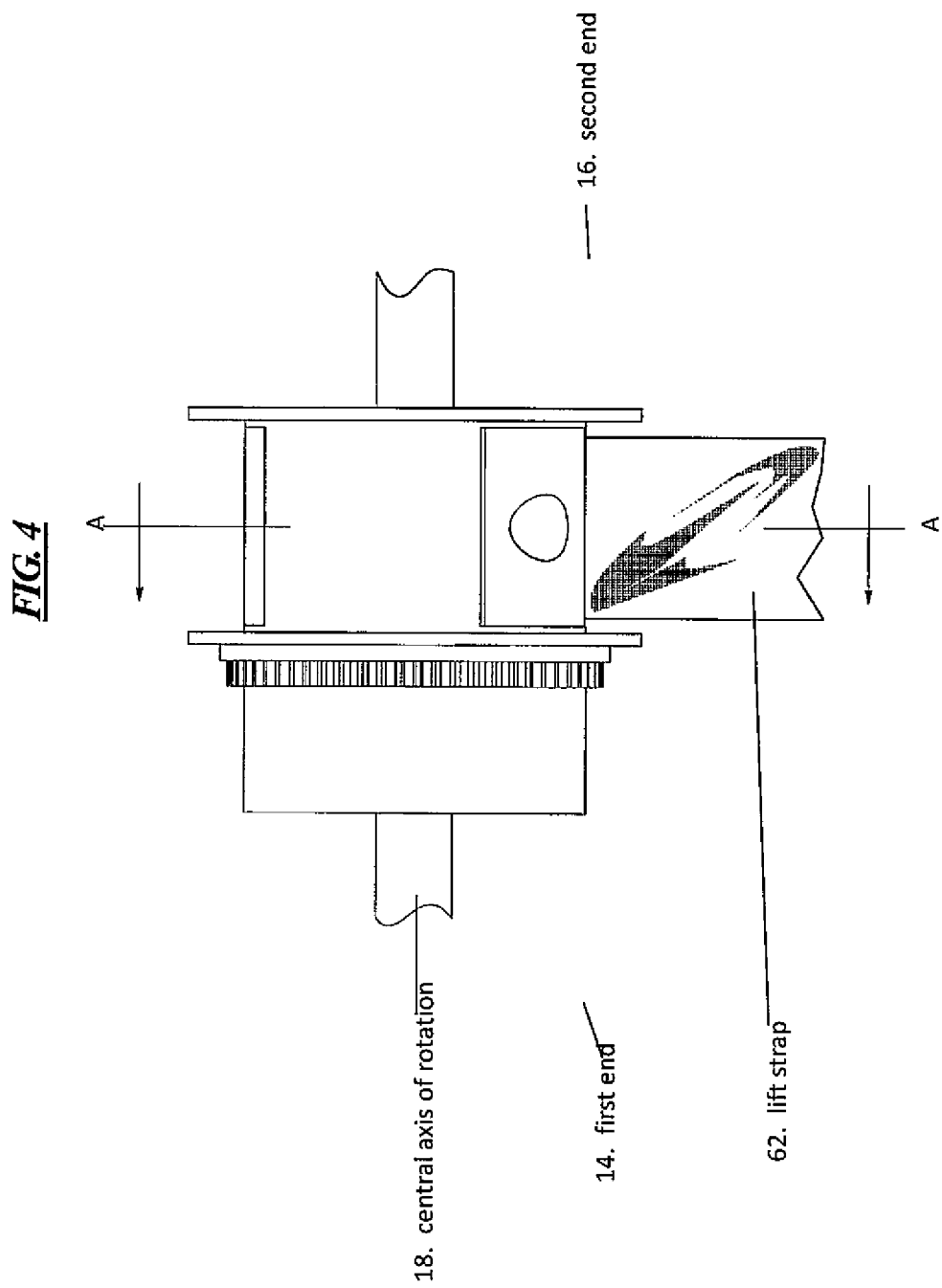
FIG. 4 is a side view of the embodiment of the split lift drum of FIG. 1.
Figure 5:
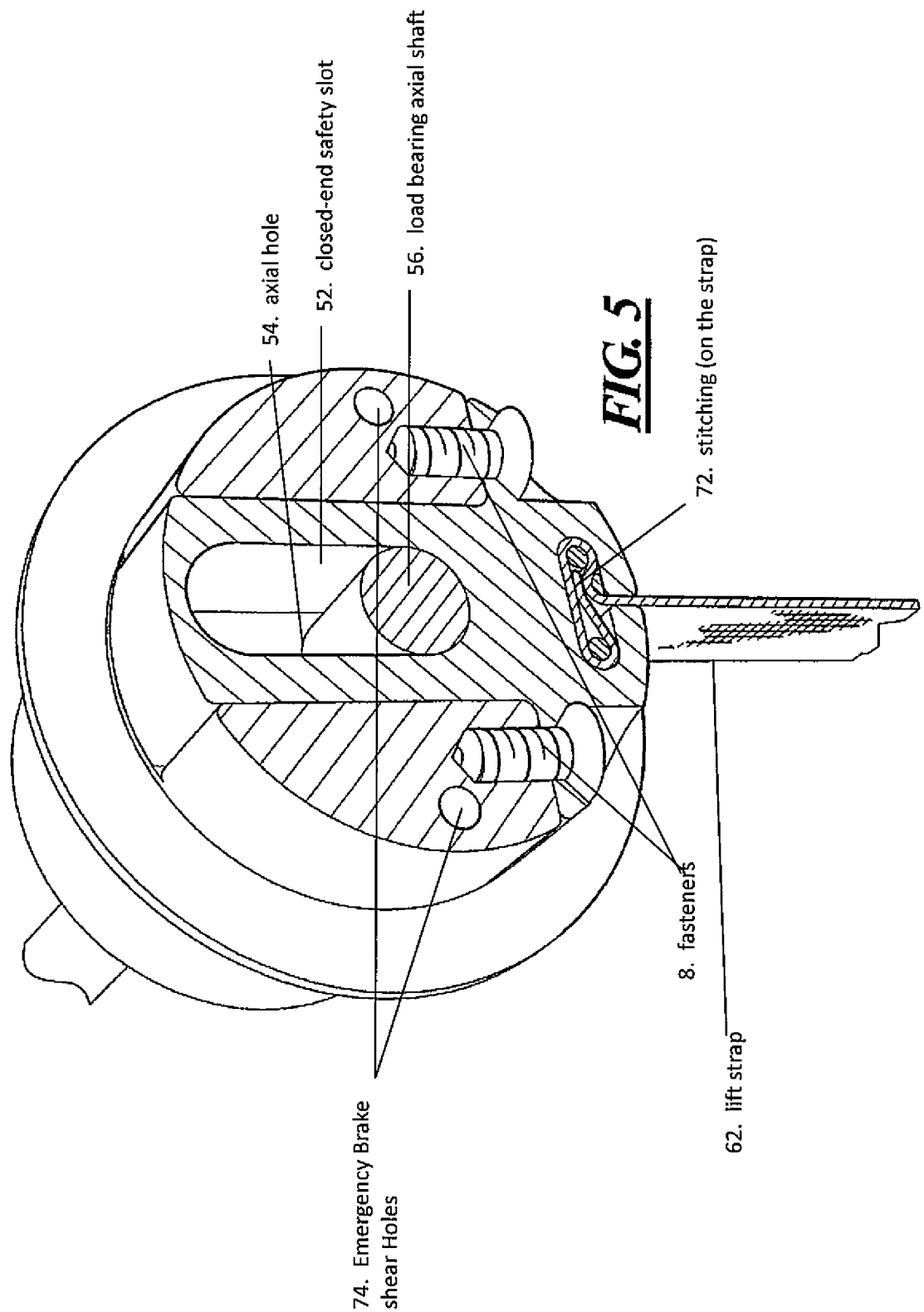
FIG. 5 is an isometric cross-section view of the embodiment of the split lift drum of FIG. 4, taken about the section line indicated in FIG. 4, showing the strap-lock slider and installed lift strap in the fully mated and secured position within the drum body.
Figure 6:
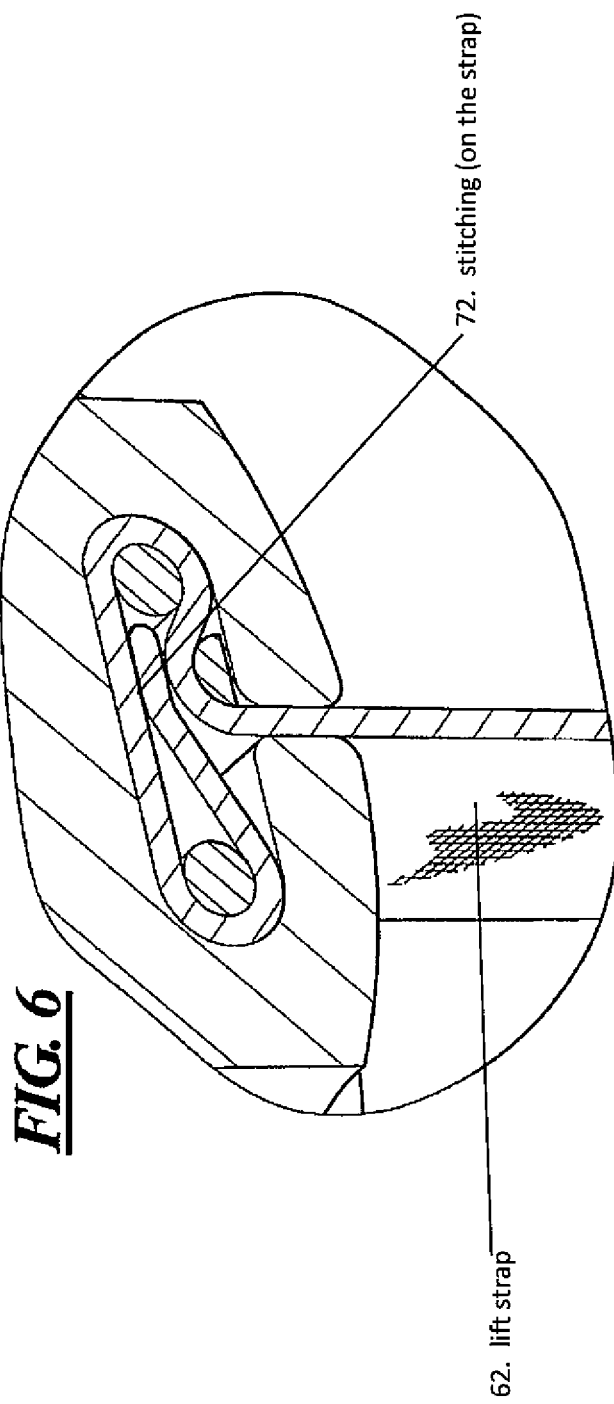
FIG. 6 is an isometric cross-section detail view of FIG. 4, showing an embodiment of the lift strap locking bar installed in the strap retention recess in the strap-lock slider.
Figure 7:
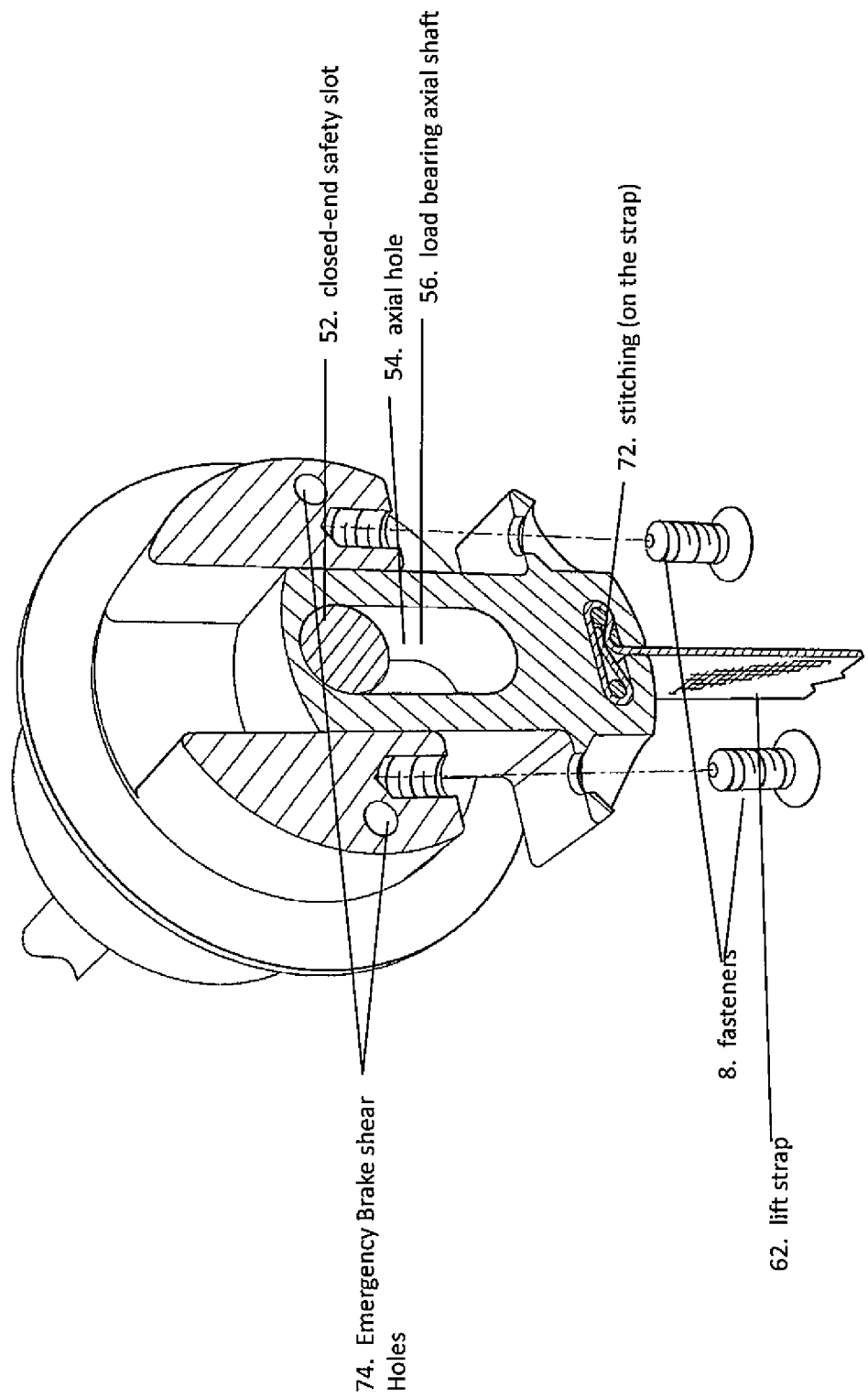
FIG. 7 is an isometric cross-section view of the embodiment of the split lift drum of FIG. 4, taken about section line A-A in FIG. 4, showing the strap-lock slider and installed lift strap in the extended position from the drum body, wherein the lift strap is accessible for replacement.
Figure 13:
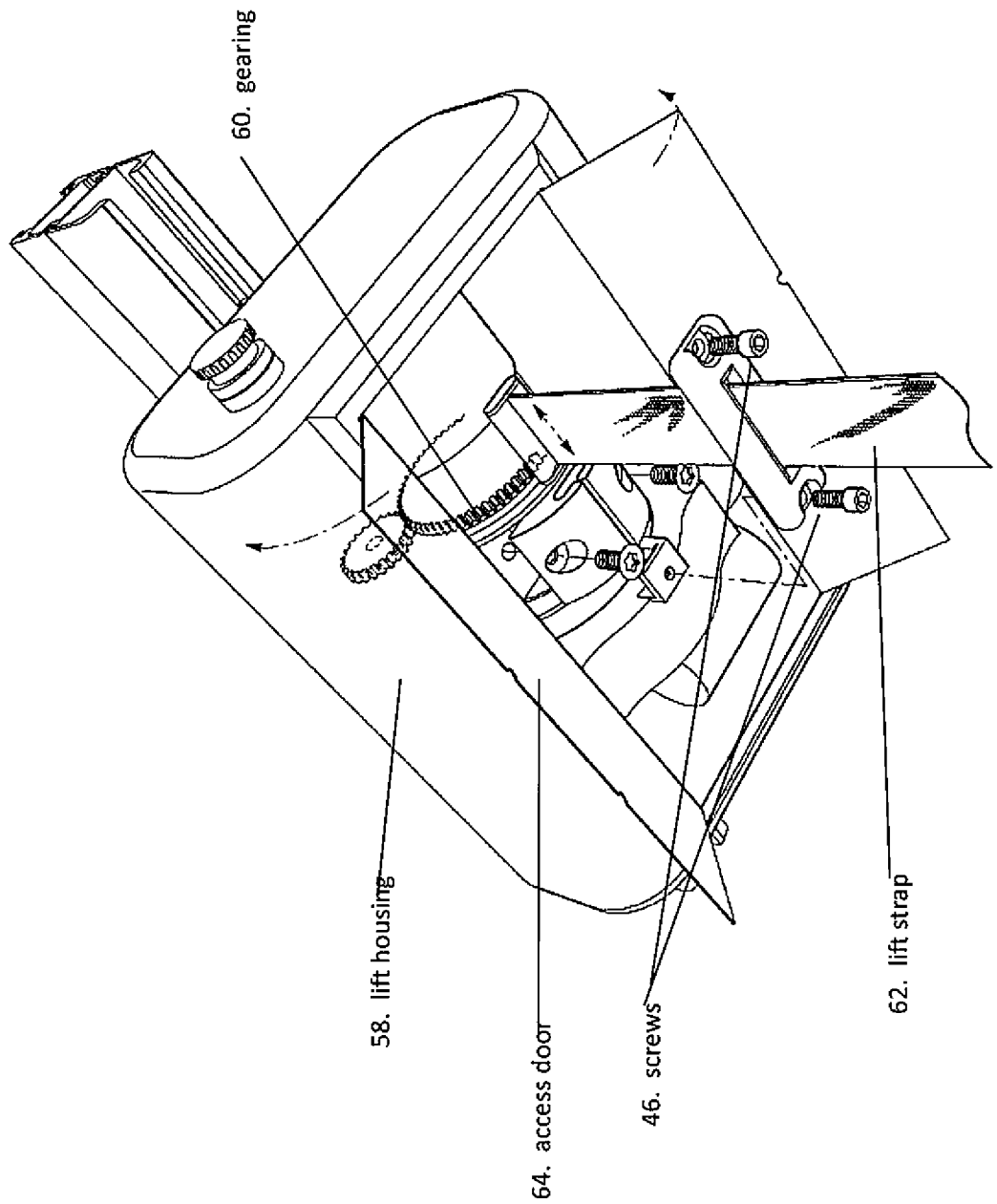
FIG. 13 is an isometric view of an embodiment of an overhead lift system of the present disclosure utilizing a split lift drum as disclosed herein, and showing an embodiment of an access door in the lift housing in an opened position to provide access to the split lift drum.

Referring to FIG. 5, the pictured embodiment of the drum body 4 shows a cross section of the drum body 4 taken through section line A-A in FIG. 4. Section line A-A is a section plane that is perpendicular to the central axis of rotation 18 and that sections through the slider channel 22 formed in the central barrel 10. In FIG. 5, it can be seen that the slider channel 22 of this embodiment is generally in the shape of an upside down "T." The "T" shape of the slider channel is formed by the perpendicular intersection of (1) a square-bottomed through-slot cut perpendicular to the rotational axis through a portion of the outer work surface of the central barrel, the slot forming the top cross member of the "T" shaped channel, and (2) a rectangular through-hole passing through the axis of rotation in the central barrel that forms the main leg of the "T" shape. In the depicted embodiment, the height of the cross member of the "T" shaped slider channel through the central barrel is approximately one-fourth of the width of the diameter of the central barrel, however in alternate embodiments, it may be of any number of different sizes.

A longitudinal centerline of the rectangular through-hole that forms the main leg of the "T" shape intersects the central axis of rotation 18 of the drum body 4. The longitudinal centerline of the rectangular through-hole also bisects the square bottomed through-slot that forms the cross member of the "T." The "T" shaped slider channel also defines a pair of drum stop-faces 26. These drum stop-faces 26 provide a positive stopping surface against which a pair of complimentary slider stop faces on the strap-lock slider 6 will rest, when the strap-lock slider 6 is mated to a fully seated position in the slider channel 22 of the drum body 4.

While the above described embodiment discloses a "T" shaped slider channel 22, this disclosure should not be read to limit the slider channel to any specific shape. Rather, in alternate embodiments, the slider channel may take additional shapes, and/or be of alternate channel types, without departing from the scope of this disclosure. For example, in an alternate embodiment the slider channel may be a blind-hole type channel having a single opening in the central barrel and traveling a specific distance into the central barrel, where the channel bottoms out within an interior of the central barrel. In still another alternate embodiment, the slider channel may be a through-hole type channel wherein the channel passes completely through the central barrel and defines a first opening on one side of the central barrel and a second opening on an opposite side of the central barrel.

In one embodiment, the slider channel 22 may have a square or rectangular cross-section when being viewed through the opening 24 of the slider channel formed in the work surface 20 of the central barrel 10. In an alternate embodiment, the slider channel 22 may have a circular or oval cross-section when being viewed through the opening formed in the work surface 20 of the central barrel 10. In still further alternate embodiments, the slider channel 22 may take any such shape that permits the strap-lock slider 6 to slidably be engaged or mated within the drum body 4.

Strap-Lock Slider

Referring to FIGS. 1-3, 5 and 7, the depicted embodiment of the strap-lock slider 6 is a generally formed as an upside down "T" shape that is complementary to the shape of the slider channel 22 in the drum body 4. In this regard, the strap-lock slider 6 includes a longitudinal slider body 28 having a first end 30 and a second end 32. Disposed at the first end of the slider body 28 are a pair of ears 34 that extend therefrom, one each, on opposite sides of the slider body. The two ears 34 on opposite sides of the slider body 28 form the cross member of the "T" shaped strap-lock slider 6. In this embodiment, the "T" shaped strap-lock slider generally has a square or rectangular outer cross section through the main leg of the "T" shape. However, as stated previously, in alternate embodiments, the cross section of the strap-lock slider will have a shape that is complementary to the shape of the slider channel in the drum body 4. Accordingly, should the slider channel in the drum body 4 be circular cylindrical in shape, then the slider body of the strap-lock slider will also be circular cylindrical in shape such that the strap-lock slider can be slidably mated into the slider channel in the drum body 4.

The opposing outer end faces 36, 38 of the first end 30 and second end 32 of the strap-lock slider, including the outer surfaces of the ears disposed at the first end 30, are convex cylindrical curved surfaces that share a common central axis and have radii that are each equal to the radius of the central barrel's outer work surface 20 in the drum body 4. In this manner, when the strap-lock slider 6 is slidably mated to a fully seated position in the slider channel 22 of the drum body 4, the outer end faces 36, 38 at the first and second ends of the strap-lock slider 6 will be flush with, and have the same curvature as, the cylindrical outer work surface 20 of the drum body 4, such that a generally complete cylindrical outer work surface is created for the split lift drum 2.

Furthermore, each of the two ears 34 of the strap-lock slider 6 defines a slider stop face 40, which stop faces are generally located opposite of the curved outer end face 36 at the first end 30 of the slider body 28. The slider stop faces 40, as described above with respect to the drum body 4, form a positive stop against which the drum stop-faces 26 will mate when the strap-lock slider 6 is in a fully seated position within the drum body 4.

In addition, disposed in the first end of the slider body is a strap retention recess 42 that runs parallel to the central axis of rotation 18 of the drum body 4. In the depicted embodiment, the retention recess is a through-hole whose cross section has parallel sides and semicircular ends. This through-hole is configured to permit a complementary shaped strap locking bar secured to the end of a lift strap 62 to be slidably mated therein. The retention recess 42 also includes a thin strap-entry slot 44 cut through one sidewall thereof that extends to and through the curved outer end face 36 at the first end of the strap-lock slider 6. The retention recess 42 has a significantly larger width than the strap-entry slot 44, which slot is generally just wider than the thickness of the lift strap 62. This thin slot 44 permits access from an interior of the retention recess 42 to an exterior of the slider body. When a strap locking pin is slid into the retention recess 42, the portion of the lift strap 62 extending from the locking pin is slid through the strap-entry slot 44 in the slider body 28, such that the end of lift strap 62 is secured into the strap-lock slider 6 while the remainder of the lift strap 62 protrudes through the strap-entry slot 44 and is located external to the strap-lock slider 6.

While the prior embodiment disclosed a strap retention recess 42 of a particular shape, it should be understood that in alternate embodiments the strap retention recess may have alternate cross-sectional shapes as needed to compliment the shape of a strap locking pin at the end of the lift strap 62 that is to be retained therein.

Fasteners

Referring to FIGS. 1-3, 5, and 7, the split drum can further include one or more fasteners 8 for retaining the strap-lock slider 6 in a fully seated and retracted position within the drum body 4. In the embodiment depicted in FIGS. 1-3, 5, and 7, the fasteners 8 are a pair of countersink screws 46 that are removeably mated through countersunk ear holes 48 located in the ears 34 of the strap-lock slider 6, and whose threaded shanks protrude from the slider stop-faces 40. The screws 46 are screwed into complementary threaded holes 50 disposed in the drum stop-faces 26 of the drum body 4. The countersunk ear holes 48 and screws 46 permit the strap-lock slider 6 to be locked in to the drum body 4 in a fully seated position without having screw heads protruding above the curved outer work surface of the combined drum body and strap-lock slider. While the above embodiment disclosed the use of screw type fasteners, it should not be read to limit the type or number of fasteners 8 that can be used to secure the strap-lock slider in a load-bearing, fully mated position within the drum body 4. In alternate embodiments, additional fastener types, such as ball-lock fasteners, shear pin fasteners, alternate threaded fasteners, bayonet type fasteners, and other similar, load-bearing fastener types, may be employed to secure the strap-lock slider in a load-bearing, fully mated position in the drum body 4.

In one embodiment, the strap-lock slider 6 may be fully slidably removable from the drum body 4 by simply removing or disengaging the fasteners 8. However, in such an embodiment, should those fasteners 8 ever break while the lift strap 62 is under load and the strap is completely unwound from the work surface, the strap-lock slider 6 could disengage completely from the drum body and drop the load at the end of the lift strap 62 to the floor rather abruptly. Accordingly, alternate embodiments of the present disclosure provide a safety mechanism, whereby even if the fasteners 8 break or become disengaged, the strap-lock slider 6 cannot be fully disengaged from the drum body 4. Accordingly, in an alternate embodiment, the strap-lock slider and drum body 4 may be configured such that, when the fasteners 8 are disengaged from the strap-lock slider 6 and the drum body 4, the strap-lock slider is able to be slidably moved within the drum body 4, but cannot be completely removed from the slider channel 22 of the drum body 4 without first removing a safety shaft inserted through both the drum body 4 and the strap-lock slider 6. In this manner, the strap-lock slider 6 is at least partially retained within the drum body 4 at all times, even when the fasteners 8 are disengaged.

Referring to FIG. 5, to create the safety mechanism and achieve the partial slidable retention of the strap-lock slider 6 within the slider channel 22 of the drum body 4, a closed-end safety slot 52 is defined in the strap-lock slider 6 and extends through opposing slider faces of the strap-lock slider 6. The safety slot 52 is a longitudinal rectangular cavity having semicircular opposite ends, however, alternate safety slot shapes may be utilized as is appropriate. An axial hole 54 is also defined through the center of the drum body 6 such that it is concentric with the axis of rotation 18. The axial hole 54 extends at least through one side of the drum body up to, and into, the slider channel 22. In alternate embodiments, the axial hole 54 may extend through the slider channel 22 and into a portion of, or completely through, the opposite side of the drum body, such that a section of the axial hole 54 is disposed in the drum body 4 on both sides of the slider channel.

The safety mechanism discussed above is created by the engagement of a load bearing axial shaft 56 through both of (1) the axial hole 54 in the drum body and (2) the closed-end safety slot 52 in the strap-lock slider 6. When the axial shaft is engaged through both of the drum body 4 and strap-lock slider 6, the load bearing axial shaft 56 permits the strap-lock slider 6 to be slidably movable within the slider channel 22 about the length of the safety slot 52, but prevents the strap-lock slider 6 from being completely removable, due to the interference between the axial shaft 56 and the closed end of the safety slot 52 that fully surrounds the axial shaft 56. Accordingly, when the fasteners 8 are disengaged, the strap-lock slider 6 may only be permitted to drop from a fully mated and operational position within the drum body 4, to an extended position within, but protruding from, the drum body 4. When the strap-lock slider is in the extended position, the first end 30 of the strap-lock slider 6 is at least partially clear of the outer edges of the end flanges 12 on the drum body 4 and the strap retention recess 42 is now accessible. Once the strap retention recess 42 is accessible, the lift strap 62's locking bar, located at the end of the lift strap 62, can be slidably removed from the strap retention recess 42 of the strap-lock slider 6 in order to replace the lift strap 62.

The above disclosure of the safety mechanism, employing an axial shaft and complimentary slot in the slider, to prevent complete removal of the strap-lock slider should not be read to limit the method or apparatuses by which the strap-lock slider is slidably retained within the drum body, but prevented from complete removal, when the fasteners are removed or disengaged. In alternate embodiments, no axial shaft may be needed to achieve such a safety mechanism or the axial movement.

For example, in an alternate embodiment, the strap-lock slider may be slidably retained within the drum body by the use of a set of toggle-type, spring loaded arms disposed in the drum body. The arms are secured in pockets within the walls of the slider channel in the drum body by hinge pins, and are biased to an extended position by torsion springs. The arms fold about the spring loaded hinges and the ends thereof engage in an interference manner within complementary pockets disposed along the slider faces of the strap-lock slider when the fasteners are disengaged and the strap-lock slide is moved to an extended position from the drum body. The interference fit prevents complete removal of the strap-lock slider from the drum body. Alternatively, the spring loaded arms may be located in pockets disposed in the spring lock slider and engage with complementary pockets in the walls of the drum body.

Another alternate embodiment has a two piece drum body, wherein one of the end flanges of the drum body is a separate piece that is secured to the drum body, and which forms one side wall of the slider channel. Upon removal of the separate end flange, one sidewall of the slider channel is removed to reveal an offset "I" shaped slider channel, whereby the upper cross member of the "I" channel is taller than the lower cross member of the "I" channel. A complementary "I" shaped strap-lock slider is mated into the slider channel through the open side of the slider channel that has been opened by the removal of the end flange. The end flange is again secured to the drum body closing up the otherwise open side of the slider channel. The top cross member of the "I" shaped strap-lock slider is shorter than the height of the top cross member of the "I" shaped slider channel. The "I" shaped strap-lock slider is thus slidably retained within in the drum body, yet can slidably move such that the bottom of the strap-lock slider is extended from the drum body. The strap-lock slider can then be slidably moved to a fully seated position in the drum body and secured in place by fasteners, thus preventing any sliding movement while the fasteners are engaged.

Emergency Brake

The lift system employing the split drum 2 may further optionally include an emergency brake to prevent free rotation of the split drum 2 in the unlikely event that the drive gearing of the split drum 2 becomes disengaged from the gearing of the driving motor. If the lift system senses that the lift drum suddenly begins paying out the lift strap 62 faster than a predetermined rate or that rotational speed of the split drum 2 exceeds a predetermined speed, the emergency brake automatically engages. The sensing of excessive speed may be done by an electronic sensor and/or programming in the controller circuitry of the lift system. Alternatively, the sensing can be performed by mechanical means such as a centripetal drive, or rhombic drive, connected to the rotating split drum, which drive acts as, or similar to, a speed governor.

In one embodiment as shown in FIG. 5, the emergency brake is a shear-pin type emergency brake, wherein one or more frame shear pins (not depicted) located external to an end of the split drum automatically spring forward to mate with and engage into at least one of a set of emergency brake shear holes 74 in the split drum. The shear holes 74 each run parallel to the central rotational axis 18 of the split drum 2 and the pins are only able to move in a direction parallel to the axis of rotation, such that when the pins engage the holes, the pins stop the split drum from rotating any further. This prevents the lift strap 62 from being paid out any further and in turn prevents the load suspended from the end of the lift strap 62 from dropping any further toward the floor. However, in alternate embodiments, alternate emergency brake systems can be employed without departing from the scope of the present disclosure.

Each of the drum body 4, strap-lock slider 6, fasteners 8, and load bearing axial shaft 56 are made from steel, aluminum, other such suitable metal or metal alloy, polymer, co-polymer, or any combination thereof, that has the needed strength, weight, and durability characteristics to handle the loads to which each such component will be subjected during use of the split drum 2 and the lift system of which the split drum 2 is a part.

Operation

Referring to FIGS. 1-3, 7, and 13, in operation, the split lift drum 2 is operably connected to a lift motor, both of which are retained inside an outer lift housing 58 and are a part of the overhead lift. The overhead lift may be secured within an overhead rail system mounted to structural components within the ceiling of a patient room, such that the lift is a moveable, overhead patient lift. The lift may alternatively be affixed to a single anchor located in the ceiling, in which case it is not a moveable patient lift, rather a stationary lift. The lift motor rotationally drives the split lift drum 2 about the drum body's central axis of rotation 18. In one embodiment, a radial bearing may be employed to aid rotational movement of the split drum 2. Such a radial bearing has a rotational axis that is collinear with the rotational axis of the drum body 4. In one embodiment, the first end of the drum body 4 includes gearing 60 that is either integral to or affixed to the drum body 4 on an outer surface of the end flange 12. The gearing is operatively coupled to complementary gearing that is either directly connected to, or driven by the lift motor. However, in alternate embodiments, worm gearing configurations, chain or belt drives, or similar such driving mechanisms may be employed to drive the split lift drum.

An operator control is utilized to input commands for controlling operation of the lift motor, and thereby the operation of the split lift drum 2. The motor can be directed to drive the gearing 60 in a first rotational direction, thereby winding up the lift strap 62 that extends therefrom and thus raising the free end of the lift strap and anyone suspended therefrom. The motor can also be directed to drive the gearing 60 in a second rotational direction opposite the first rotational direction, thereby paying out the lift strap 62 from the split drum 2 and lowering the free end of the lift strap and anyone suspended therefrom.

When it is necessary to replace the lift strap 62 in the overhead patient lift, either due to damage/wear to the lift strap, routine maintenance, or for any other reason, replacement is simplified by use of the split lift drum 2. To replace the lift strap 62 extending from the bottom side of the overhead lift, any active load is removed from the free hanging end of the lift strap 62 and the motor rotates the split lift drum 2 such that it pays out the full available length of the lift strap 62, leaving the strap extending radially outward from the outer work surface 20 of the split lift drum 2. With the lift strap 62 fully unwound and extended from the split lift drum 2, the slider channel 22 and complementary strap-lock slider 6 are oriented vertically with respect to the direction of sliding motion, such that they are placed in the upside down "T" position. In such a position, once the fasteners 8 are disengaged, the strap-lock slider 6 is slidably moveable to an extended position from the drum body 4 in the downward vertical direction. To gain access to the split drum 2, an access door 64, disposed in a bottom side of the lift housing 58 and surrounding the protruding lift strap 62, is opened. Opening the access door 64 provides access to the fasteners 8 that secure the strap-lock slider 6 in the fully seated and secured position within the drum body 4 of the split drum 2. In one embodiment, the access door 64 in the bottom of the lift housing 58 may be a single door hinged with respect to the remainder of the lift housing 58. In alternate embodiments, the access door 64 may be pair of hinged access doors, a removable snap-fit panel, a sliding panel, a flexible sliding roll-up type retractable panel, or any other type of cover for an access opening that provides selectable access to the split drum 2 insode the lift housing 58.

With the access door 64 opened or removed from the lift housing 58, the fasteners 8 are exposed. The fasteners 8 are next removed or disengaged, as the case may be, to permit the strap-lock slider 6 to slidably drop vertically downward in relation to the drum body 4, to an extended position directed radially outward from the drum body 4. In the depicted embodiment, the fasteners 8 are a pair of screws 46 that are unscrewed and removed from the ears 34 of the strap lock slider 6. Once the strap-lock slider 6 is in an extended position, the strap retention recess 42 is extended in a radial direction away from the axis of rotation 18 such that it is located farther from the axis of rotation 18 than the outer edge of the end flanges 12. Therefore, the slider's retention recess 42 is clear of the end flanges 12 of the drum body 4, and a strap locking bar 66 affixed to the end of the lift strap 62 may be slidably disengaged from within the strap retention recess 42 of the strap-lock slider 6. In this manner, the lift strap 62 has been removed from the overhead lift for replacement.

With the old lift strap removed, a new lift strap 62 is installed by sliding the strap locking bar 66 secured to the end of the new replacement lift strap into the retention recess 42 of the strap-lock slider 6 in a direction parallel to the central axis of rotation 18 of the split drum 2. In doing so, the portion of the lift strap 62 extending from the locking bar 66 is also inserted into the strap-entry slot 44 in the slider 6 and extends outward and downward form the strap-lock slider 6. Once the strap locking bar 66 is fully seated within the strap retention recess 42, the strap-lock slider 6 may be pushed vertically upward such that it is retracted within the drum body 4 and is again located in its fully seated position within the drum body 4. In this position, the drum stop faces 26 are mated against, and flush with, the slider stop faces 40, while the curved end faces 36, 38 of the strap-lock slider 6 are flush, and in alignment, with the outer work surface 20 of the drum body 4. This creates a continuous outer work surface without any significant gaps therein. The fasteners 8 are re-engaged thereby securing the strap-lock slider in the fully seated position within the drum body 4. In the depicted embodiment of FIG. 1 the fasteners 8 are a pair of screws 46 that are inserted through the countersunk holes 48 in the ears 34 of the strap-lock slider 6 and screwed into complementary threaded holes 50 in the drum body 2. The access door 64 in the lift housing 58 is secured back in place, and the motor may drive the split drum 2 to rotate and wind up the extended lift strap 62 around the outer work surface 20 of the split lift drum 2. The lift strap has thus been replaced in a much more expedient manner as compared to current lift systems and techniques, and the overhead lift is then ready for continued use.

Strap Locking Bar

Referring to FIGS. 5-7, 11, and 12, the strap locking bar 66 disposed at the end of the lift strap 62 that secures the lift strap 62 within the strap-locking slider 6 may be a single mandrel or pin, around which the end of the end of the lift strap 62 is tightly wrapped and secured back onto itself either by stitching or other similar securing mechanism. In this manner, the lift strap 62 forms a loop of material at its end with the mandrel held tightly inside of the resulting loop. However, in an alternate embodiment, the strap locking bar 66 is comprised of a series of pins 68, for example three parallel pins that are each mated at their ends to the inner facing surfaces of parallel first and second end plates 70, such that the axes of the pins are perpendicular to the parallel surfaces of the plates. The end of the lift strap 62 is wrapped around one of the pins and secured back onto itself using bartack stitching 72 or other securing method, while the adjoining portion of the lift strap is woven around and through the remaining series of pins.

The lift strap 62 exits this labyrinth of pins that comprise the strap locking bar 66 at a point after which the strap has been at least partially woven around or past each of the individual pins, making some contact with the outer surface of each pin. The purpose of weaving the lift strap 62 around each in a series of pins 68 is to provide friction between the lift strap 62 and the outer surface of each pin 68. By doing so, if the split lift drum 2 is ever in a position where the lift strap 62 is completely unwound from the work surface of the split lift drum 2 while an active load is suspended from the free end of the lift strap 62, then the entire force of the active load is not being supported solely by the stitching or other securing mechanism used to secure the strap 62 back on to itself. The friction provided by the lift strap 62 woven around and through the series of pins 68 serves to lessen the load and active stresses that would otherwise be placed on the stitching.

Coated Lift Strap & Protective Sleeve

Referring to FIGS. 9 and 10, the lift strap 962 used with the strap locking bar 66, the lift drum and overhead lift 907 may be any type of strap that is approved for medical lifting of patients or other loads. For example, the lift strap may be woven textile, such as woven polyester or nylon as is commonly used with patient lifts. In alternate embodiments, the lift strap may be a woven textile strap that has been chemically treated and/or polymer-coated to provide increased infection control to the lift system and lift strap 962. A polymer coated lift strap for infection control may comprise a base lift strap, such as a woven polyester textile strap, any number of antibacterial chemical treatments applied to the base lift strap to impregnate the chemical treatment within the individual fibers of the woven base lift strap, and any number of polymer coatings applied thereafter that encase the chemical treated woven base lift strap in one or more layers thereof.

In one embodiment, an infection control lift strap comprises a woven polyester base lift strap that has been treated with a chemical, such as Aegis antimicrobial coating treatment or Maedical i-LiNK advanced antimicrobial treatments developed by Devan Chemicals N.V., which, for example, chemically bonds to the fibers of the woven base lift strap and creates a life-long protection against various microorganisms and bacteria, including *Clostridium Difficile*, more commonly referred to as C. Diff. The embodiment of this lift strap 962 could additionally include a disinfectant-safe coating 950 applied over the chemically treated base lift strap, such that disinfectants can be regularly used on the lift strap 962 without damaging or altering the chemical bond that exists between the chemical treatment and the base lift strap.

In another embodiment, an infection control lift strap 962 may be a woven textile lift strap that has one or more layers of a non-porous wipeable polymer overcoating, such as the BioThane Coated Webbing brand coated strap products developed by BioPlastics Company Inc. In yet another embodiment, an infection control lift strap may be a solid strap that is flexible, non-porous, and chemically wipeable, wherein the lift strap 962 is neither a woven strap nor needs any overcoating to be wipeable with chlorinated bleach or other sanitization products.

In still other embodiments, the lift strap 962 can include any combination of a solid base strap or a woven textile base strap, one or more chemical treatments applied thereto, and/or one or more outer overcoating layers that encapsulate the lift strap therein (e.g., the base strap and the chemical treatment applied) and that are impermeable to chlorinated bleach or other harsh cleaning or disinfection solutions. For example, an overcoating 950 could include coatings of either polyurethane, polyvinyl chloride (PVC), or other such polymers that completely seal the base strap therein and are able to be wiped down with chlorinated bleach or other such harsh antibacterial or cleaning solutions. The overcoating 950 used with a woven lift strap 962 would fill in all the small crevices and spaces between the fibers of the woven lift strap and provide a continuous sealed outer surface without any crevices or spaces in which chlorine crystals could form when chlorinated bleach used to clean the lift strap dries. Any such crystals would form on the outer surface of the overcoating 950 and not cause damage to the base lift strap 962.

In addition, a disposable or washable flexible protective sleeve 902 could be used with the lift strap 962 to increase infection control properties with regard to the overhead lift 907, the lift strap 962, and the inner workings of the overhead lifts 907. Such a protective sleeve 902 would serve to prevent bacteria or other contaminants from ever reaching the lift strap 962 while the sleeve 902 is in place.

In one embodiment, a protective sleeve 902 comprises a flexible elongated tubular polymer sleeve, having double sided adhesive strips 904 disposed at both ends thereof around the full circumference of the openings of the sleeve. One side of the double sided adhesive tape 904 would be secured to an inner surface of the outer sleeve at the open ends thereof and have a removable backing paper disposed on the opposite side of the double sided adhesive strip 904. The sleeve 902 could be slid over the free hanging end 908 of the lift strap 962 in an overhead lift 907. A first end of the protective sleeve 910 is slid over the free end of the lift strap 908, such that the lift strap 962 is located inside of the tubular sleeve 902 and the first end 910 is the uppermost end of the sleeve relative to the hanging lift strap 962. The first end of the sleeve 910 is then positioned such that it is located adjacent the housing 957 of the overhead lift 907. The removable backing strips on the adhesive tape 904 located at the upper end of the protective sleeve 902 are then removed, and the upper end of the protective sleeve 902 can then be sealingly secured to the lift housing 957 around the slot 959 in the housing from which the lift strap 962 protrudes.

The lower end of the protective sleeve 912 is then secured by its adhesive tape to either the solid lifting fixture secured to the free end of the lift strap 908, or to a sling bar 973 that is secured below the lifting fixture. With the upper end of the protective sleeve 910 sealingly secured to the lift housing 957 and the lower end of the protective sleeve 912 sealingly secured to the lifting fixture, or sling bar 973, the lift strap 962 is fully sealed within the protective sleeve 902. Thus, no bacteria or other contaminants are able to gain access to the lift strap. With the use of a protective sleeve 902 as disclosed herein, the frequency with which the lift strap 902 needs to be cleaned or sanitized is significantly reduced, or the need to clean the lift strap 962 is altogether eliminated. In this manner, the useable life of the lift strap 962 can be significantly extended.

A protective sleeve 902 for use with the lift strap as disclosed herein is thin and flexible and will easily bunch and straighten out along its length as the lift strap 962 is either wound up on the lift drum in the lift housing 957, or paid out therefrom. The lift strap 962 can be disposable and made from any polymer, especially any polymer that when extruded into a thin tubular sleeve is impermeable to bacteria and other microscopic contaminants. After use, the disposable protective sleeve 902 is simply removed and discarded and a new sterile protective sleeve 902 can be installed in its place. In alternate embodiments, the protective sleeve 902 can be a washable textile-based sleeve, or a textile-based sleeve having a sealed outer surface, both of which are capable of being washed, sterilized, and reused.

What is claimed is:

1. A patient lift, comprising:
   a motor;
   a two-piece lift drum operatively driven by the motor, the two-piece lift drum comprising:
      a drum body having one or more partial cylindrical outer work surfaces;
      a strap-lock slider comprising:
         a first end and a second end;
         one or more partial cylindrical outer work surfaces; and
         a lift strap retention pocket disposed near the first end, the strap-lock slider being slidably secured within the drum body;

one or more fasteners configured to secure the strap-lock slider in a retracted position in relation to the drum body;

wherein when the one or more fasteners are engaged to secure the strap-lock slider in the retracted position in relation to the drum body, the one or more partial cylindrical outer work surfaces of the drum body and the one or more partial cylindrical outer work surfaces of the strap-lock slider are aligned to form a substantially continuous cylindrical outer work surface; and a lift strap comprising a first end secured to the two-piece lift drum within the lift strap retention pocket, wherein the lift strap is configured to be wound around the one or more partial cylindrical outer work surfaces of the two-piece lift drum.

2. The patient lift of claim 1, further comprising a strap locking bar secured to the first end of the lift strap and slidably disposed within the lift strap retention pocket.

3. The patient lift of claim 2, wherein the strap locking bar comprises:
a series of pins; and
first and second end plates disposed at either end of the series of pins, wherein the lift strap is wrapped around the series of pins.

4. The patient lift of claim 1, wherein the strap-lock slider further comprises a slider body defining the first end and the second end and a pair of ears extending from opposite sides of the slider body.

5. The patient lift of claim 4, wherein the one or more fasteners extend through an ear of the pair of ears.

6. The patient lift of claim 4, wherein each ear of the pair of ears defines a slider stop face that mates with a drum stop face of the drum body when the strap-lock slider is in the retracted position.

7. The patient lift of claim 1, wherein the lift strap retention pocket extends parallel to a central axis of rotation of the drum body.

8. The patient lift of claim 1, the drum body comprising:
a central barrel defining the one or more partial cylindrical outer work surfaces; and
end flanges disposed at each of a first end and a second end of the central barrel.

9. The patient lift of claim 8, wherein the lift strap retention pocket is positioned between the end flanges when the strap-lock slider is positioned in the retracted position, and is positioned past the end flanges when the strap-lock slider is positioned in an extended position.

10. The patient lift of claim 8, wherein the end flanges have a larger outer diameter than the central barrel.

11. The patient lift of claim 1, wherein the lift strap is coated with a disinfectant-safe coating.

12. The patient lift of claim 1, further comprising a lift housing, housing the motor and the two-piece lift drum, and comprising an access door removable to provide access to the one or more fasteners and the strap-lock slider.

* * * * *